United States Patent [19]
Achter et al.

[11] Patent Number: 5,528,036
[45] Date of Patent: Jun. 18, 1996

[54] SPECTRAL DETECTION OF CONTAMINANTS IN CONTAINERS

[75] Inventors: Eugene K. Achter, Lexington; John S. Beaty, Belmont; Helmut W. Klotzsch, Groton; Craig D. Thompson, Natick, all of Mass.

[73] Assignee: Thermedics Detection, Inc., Waltham, Mass.

[21] Appl. No.: 198,217

[22] Filed: Feb. 17, 1994

[51] Int. Cl.⁶ .................................................. G01N 21/90
[52] U.S. Cl. .................................. 250/339.12; 356/413
[58] Field of Search .................. 250/339.12, 339.06, 250/339.07, 339.09; 356/413, 409, 337

[56] References Cited

U.S. PATENT DOCUMENTS

| | | | |
|---|---|---|---|
| 4,221,961 | 9/1980 | Peyton | 250/223 B |
| 4,459,023 | 7/1984 | Reich et al. | 356/237 |
| 4,490,042 | 12/1984 | Wyatt | 356/340 |
| 4,551,627 | 11/1985 | Reich | 250/339 |
| 4,830,192 | 5/1989 | Plester et al. | 209/3.1 |
| 4,858,768 | 8/1989 | Plester | 209/3.1 |
| 4,998,824 | 3/1991 | Littlejohn et al. | 356/407 |
| 5,002,397 | 3/1991 | Ingrum et al. | 356/407 |
| 5,067,616 | 11/1991 | Plester et al. | 209/3.1 |

*Primary Examiner*—Davis L. Willis
*Assistant Examiner*—Richard Hanig
*Attorney, Agent, or Firm*—Fish & Richardson

[57] ABSTRACT

To spectrally detect a contaminant in a moving container, a set of reference spectral information related to one or more containers having known contents is stored. Thereafter, radiant energy is directed at liquid near the bottom of the container so that the radiant energy is modified by the contents of the container and travels through the contents of the container in multiple paths of varying length. Spectral information from detected portions of the modified radiant energy is obtained, and is compared to the stored set of reference spectral information using correlation techniques. Based on the relationship between this spectral information and the stored set of reference spectral information, the presence or absence of a contaminant is indicated.

47 Claims, 3 Drawing Sheets

SPECTRAL DETECTION OF CONTAMINANTS IN CONTAINERS

BACKGROUND OF THE INVENTION

The invention relates to spectrally detecting a contaminant in a container.

The popularity of refillable containers has increased as the costs, both social and financial, associated with disposal of packaging have become less acceptable. For example, in many countries, water and other beverages are sold in refillable bottles. These bottles are often made from a type of plastic known as polyethylene terephthalate.

After use, refillable containers are returned to a bottling plant where they are cleaned and inspected before being refilled. This inspection, in addition to checking for physical damage such as cracks, screens the containers to eliminate those that include contaminants that might degrade the flavor, safety, or other qualities of the product that they contain. The risk of contamination is greater when a container is made from plastic, as opposed to glass, because some contaminants can be absorbed into the plastic walls of the container. Absorbed contaminants can persist despite cleaning procedures, and can later leach into the product.

Though some contaminants, such as detergents and fabric softeners, are visibly colored and can be detected by human inspectors, such human visual inspection is undesirable when bottles or other containers are moving on high speed conveyors and stopping or touching the bottles to perform an inspection is undesirable or overly expensive. Moreover, such human visual inspection is subject to lapses in attention by the inspectors.

As an alternative, it has been suggested to use spectrophotometric instrumentation to automatically detect colored contaminants. Spectrophotometric instrumentation for color detection is well known in many fields, including laboratory analysis of chemical solutions, and quality control functions in the paint, fabric, and photographic industries. In general, spectrophotometric analysis of liquid samples is based on Beer's Law, which states that the optical density (i.e., the log ratio of transmitted or detected light intensity to incident light intensity) is directly proportional to the concentration of the chemical compound giving rise to the absorption of light. Beer's law is discussed, for example, in H. A. Strobel, *Chemical Instrumentation*, pp. 148–53 (1960, Addison Wesley, Reading, Mass.). Beer's law is limited in that it can only be applied if all of the detected light travels the same distance through the absorbing medium. In chemical spectrophotometric analysis, this is done by placing the liquid sample in a cuvette, or optical cell, having parallel windows that are typically spaced apart by ten millimeters.

When a container is mostly filled with liquid, a narrow optical beam can be directed radially through the container so that it intersects the major vertical axis of the container in a region where the wall of the container is substantially parallel to the major vertical axis. In the case of a cylindrical container such as a bottle, if the beam is very narrow relative to diameter of the bottle, all of the detected light travels over substantially the same path length through the bottle, and the geometrical conditions for Beer's law are satisfied. As an alternative, the beam can be directed through the bottom of the bottle (i.e., from the bottom of the bottle to the top of the bottle, or from the top of the bottle to the bottom of the bottle).

However, when a bottle or other container only contains a few millimeters of residual liquid, it becomes much more difficult to satisfy Beer's law. For example, in refillable plastic beverage bottles, the walls of the bottle curve inward near the bottom of the bottle and are not parallel to the major axis of the bottle. Also, many refillable plastic bottles include a dome in the bottom of the bottle. In these situations, when light is directed through the side of the bottle, refraction and reflection result in the detected light travelling over a variety of path lengths, and use of Beer's law is not practical. Similarly, when light is directed through the bottom of the bottle, the length of the path that the light takes through the liquid is likely to be insufficient to allow accurate detection.

One way of dealing with small amounts of residual liquid is to mechanically tilt the bottle to pool the residual liquid in a corner of the bottle and arrange the incident beam of light perpendicular to the face of the bottle to minimize refractive effects. In this case, as long as the beam of light is sufficiently thin and the dome avoided, the path length will be well defined and free of multiple reflections, and conventional Beer's law analysis may be useful.

SUMMARY OF THE INVENTION

The invention features detection of contaminants in a moving container by extracting and examining spectra of the container and contents thereof, without requiring uniform optical path lengths or relying on an analysis under Beer's law. According to the invention, contaminants in a container moving at high speed are detected without requiring the mechanical complexity associated with tilting the container, even when the container includes only a minimal amount of liquid.

In one aspect, generally, the invention features automatic spectral detection of contaminants in a moving container. Preferably, liquid is added to the container to ensure the presence of a minimal amount needed for proper detection. Spectral characteristics of the liquid are determined by subjecting the container and the liquid to radiant energy and obtaining a resulting spectrum. This spectrum, which is derived from radiant energy that travels through the liquid in multiple paths of varying length, is then compared against a library of stored reference spectra to determine whether contaminants are present. If contaminants are determined to be present, the container is rejected.

For improved performance, two spectra are obtained for each container, and each is compared to corresponding reference spectra. The spectra are obtained, for example, by measuring a first spectrum when a container is located in a first position, moving the container to a second position, and measuring a second spectrum. In this approach, the two spectra can be obtained using only a single source of radiant energy and a single detector.

Typically, the source of radiant energy and the detector are angled relative to each other (i.e., the source of radiant energy and the detector are not coaxial), and are positioned so that the radiant energy that passes from the source to the detector passes through a region substantially near the bottom of the container. The preferred range for this angle is from 100° to 140° with the most preferred angle being at about 120°.

The amount of liquid and the concentration of contaminants in a container can vary to a large degree. Thus, to avoid falsely rejecting uncontaminated containers, features of the spectra that are relatively unaffected by variations in liquid level or concentration are employed.

In a preferred embodiment of the invention, the spectra employed are an "absorption" spectrum, which provides a measurement of the radiation absorbed by the liquid and any contaminants therein, and a "reflection" spectrum, which provides a measurement of the radiation reflected by the liquid and any contaminants therein. While the absorption spectrum and the reflection spectrum each provide accurate contaminant detection, improved accuracy of detection is achieved through use of both spectra.

The library of reference spectra against which the measured spectra are compared can include spectra associated with only uncontaminated containers, only contaminated containers, or both contaminated and uncontaminated containers. When the library includes spectra for only uncontaminated containers, the presence of a contaminant is indicated when the spectra of the container differs from all of the spectra in the library by a predetermined threshold. When the library includes spectra for only contaminated containers, the presence of a contaminant is indicated when the spectra of the container matches, within a predetermined threshold, a spectrum from the library. Finally, when the library includes spectra for both contaminated and uncontaminated containers, the presence of a contaminant is indicated when the spectra of the container differs from each of the reference spectra associated with an uncontaminated container by more than a predetermined threshold or matches, within a predetermined threshold, a reference spectrum associated with a contaminated container.

Generally, only a small amount of liquid is added to a container prior to directing radiant energy into the container. In some applications, this amount is less than ten milliliters. Often, only four and a half milliliters are used. Typically, water or a dilute aqueous solution is the liquid added.

Various forms of radiant energy can be used in generating the spectra. In certain applications, either visible light, infrared energy, or a combination of the two are preferred.

The invention is particularly useful for detecting contaminants in clear plastic bottles, such as those made from polyethylene terephthalate. However, the invention is also useful in detecting contaminants within other types of containers, containers made from other materials, and tinted containers. Generally, the only limitation on suitable containers is that they be made from materials that are translucent to the radiant energy being employed.

In another aspect, generally, the invention features a spectral contaminant detection system that includes a radiant energy source or illuminator that directs radiant energy at a container, a detector that detects radiant energy from the illuminator that has been modified by the contents of the container and produces spectral information related to the detected radiant energy, and a processor that compares spectral information from the detector with a library of reference spectra and indicates the presence or absence of a contaminant based on the relationship between the spectral information and the reference spectra. This system, which is preferably entirely automated, works effectively even when containers are moving past the system at rates on the order of 400 containers per minute or greater.

To ensure that spectral information is obtained from the detector at proper times, the system can include a first position sensor and a second position sensor that signal the processor when a container is in, respectively, a first position or a second position. The processor responds to the signal from the first position sensor by obtaining first position spectral information from the detector, and to the signal from the second position sensor by obtaining second position spectral information from the detector. The processor then compares the first and second position spectral information against a library of reference spectra to determine whether a contaminant is present.

The system preferably is positioned downstream of a liquid supplier that adds a quantity of liquid to the container before the container arrives at the illuminator. To minimize the amount of liquid required, the illuminator and detector are positioned so that radiant energy from the illuminator reaches the detector after passing through a region substantially near the bottom of the container. Typically this region is within one inch, and often within one quarter of an inch, of the bottom of the container.

Other features and advantages of the invention will be apparent from the following description of preferred embodiments, and from the claims.

DESCRIPTION OF PREFERRED EMBODIMENTS

Figure 1:
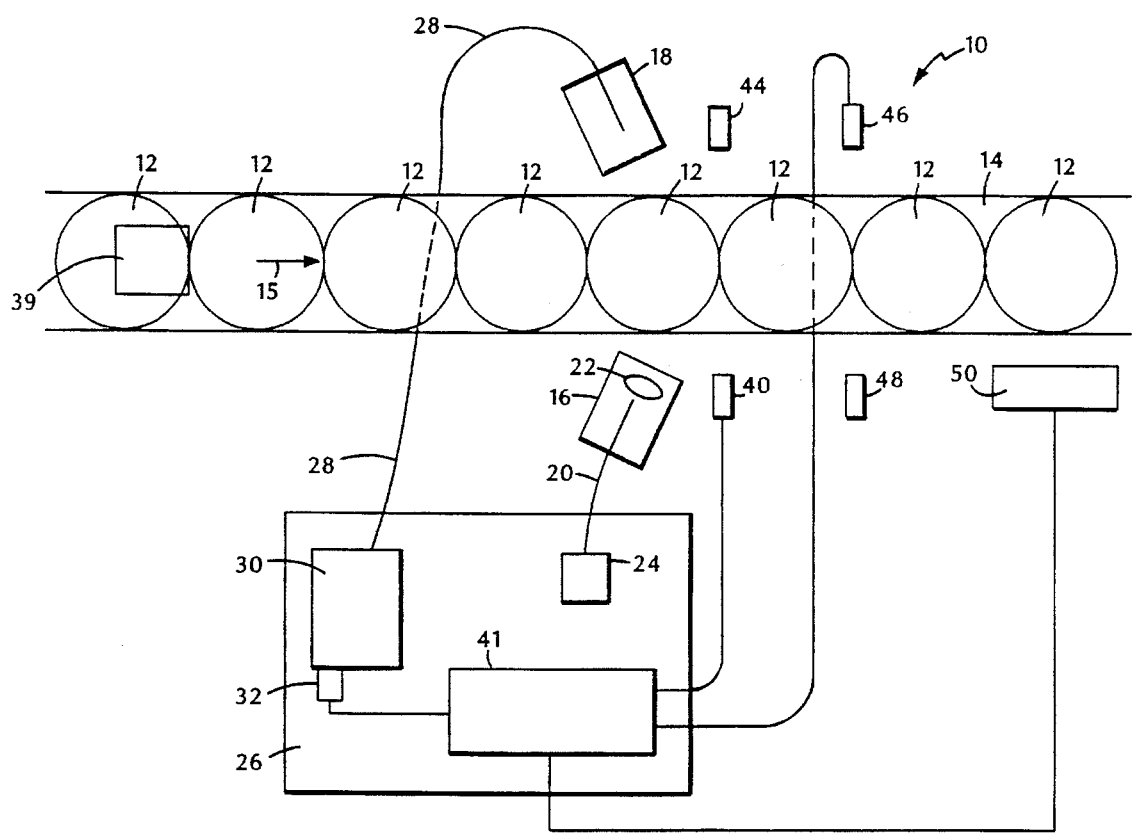
FIG. 1 is a schematic plan view of a portion of a bottle conveyor with a spectral contaminant detection system.

With reference to FIG. 1, a spectral contaminant detection system 10 is positioned to detect contaminants in containers, such as bottles 12, by analyzing spectral characteristics of liquids contained in the bottles 12, as the bottles 12 move along a conveyor 14 in the direction indicated by arrow 15. Because contaminants may be present as liquids in the bottles 12 or may leach or desorb from walls of the bottles 12 into liquids contained therein, the spectral characteristics of the liquids indicate the presence of such contaminants. Thus, by comparing the spectral characteristics of a bottle 12 and the liquid contained therein to characteristics of bottles containing contaminated or uncontaminated liquids, system 10 determines whether contaminants are present in the bottle 12.

As used herein, "contaminant" means any substance that can be detected in a container by the detection system of the invention and whose presence is incompatible with the product with which the container is to be filled. For example, detergents are contaminants with respect to beverage containers, and flavored beverages may be contaminants with respect to bottled water.

System 10 includes a radiant energy source or illuminator 16 and a detector 18. Illuminator 16 is positioned to direct radiant energy at a bottle 12 so that the radiant energy encounters liquid contained in the bottle 12. Detector 18 is positioned to detect radiant energy from illuminator 16 after that radiant energy has encountered the liquid contained in bottle 12.

Illuminator 16 includes a fiber optic bundle 20 coupled to a lens 22. Fiber optic bundle 20 transmits radiant energy from a lamp 24 located in a control unit 26 to lens 22, which focusses the radiant energy and directs the focussed radiant energy toward a bottle 12. The lamp 24 is typically a halogen lamp, but other sources of radiant energy such as, for example, a xenon flashtube that is controlled to strobe at appropriate times, could be used.

Detector 18 includes an optic fiber bundle 28 that receives some of the radiant energy from lens 22 after it has encountered liquid in the bottle 12. Fiber optic bundle 28 transmits the radiant energy to an optical spectrometer 30 in control unit 26. Within optical spectrometer 30, a series of mirrors focusses the transmitted radiant energy on a diffraction grating that separates the transmitted radiant energy into wavelength components and directs each wavelength component to a different pixel of a linear detection array 32. Typically, linear detection array 32 is implemented as a diode array or a charge coupled device ("CCD") having about one thousand pixels.

Use of fiber optic bundles 20 and 28, which may be two meters or greater in length, allows control unit 26 to be positioned a substantial distance away from the conveyor 14 and bottles 12, and thereby minimizes the exposure of control unit 26 to the potentially wet or otherwise hostile environment at conveyor 14.

Figure 3:
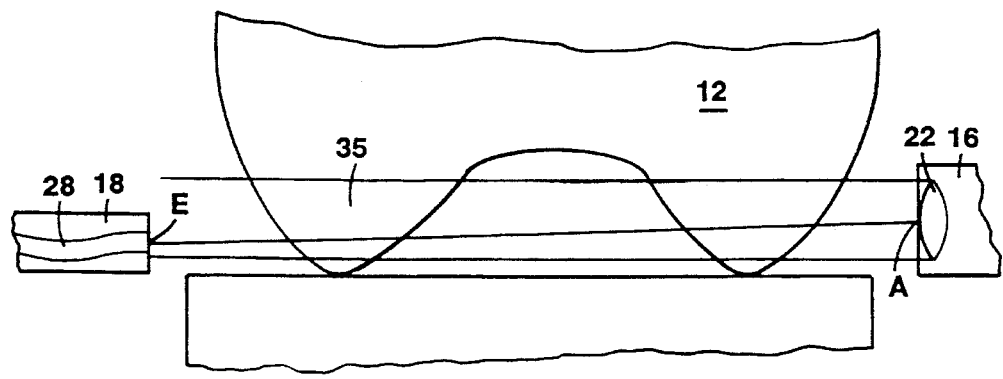
FIGS. 2 and 3 are side views of a bottle and sensors of the system of FIG. 1.
Figure 2:
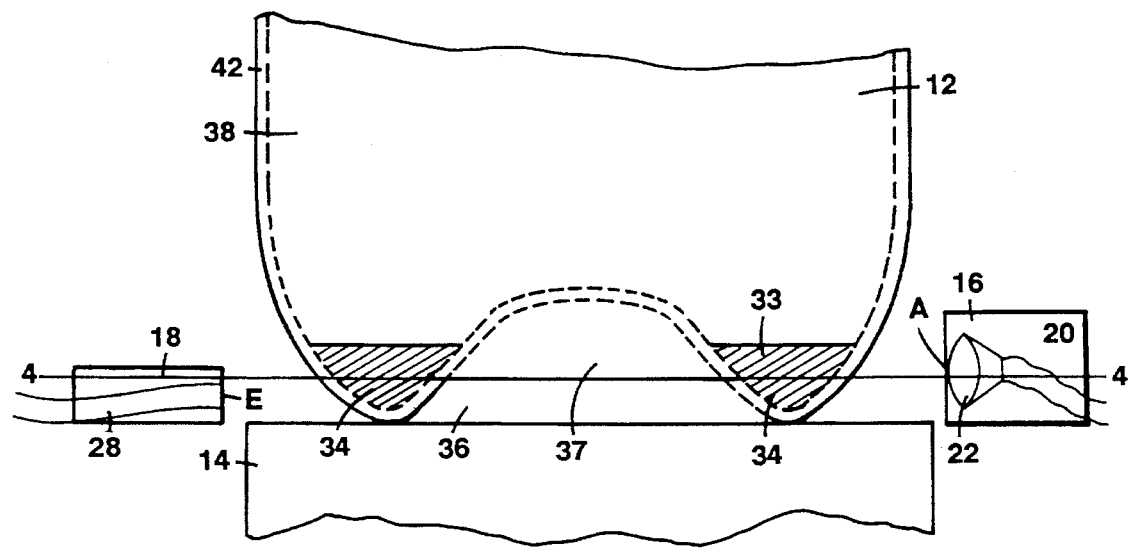

With reference to FIGS. 2 and 3, illuminator 16 and detector 18 are positioned so that the radiant energy from lens 22 is directed at a region 33 near the bottom of each bottle 12, with lens 22 being centered about one half inch above the bottom of bottle 12 and fiber 28 being centered about one quarter inch above the bottom of bottle 12. Illuminator 16 and detector 18 are aimed such that their axes of emission and reception are not aligned (i.e., illuminator 16 and detector 18, respectively, emit and receive radiation in directions that are not parallel to each other) and are not normal to the direction of movement of bottles 12 (see FIGS. 1, 4, and 5). This positioning requires the presence of only minimal amounts of liquid 34 in bottle 12. In the preferred embodiment, each bottle 12 needs to contain as little as about four and one half milliliters of liquid 34. In addition to being positioned near the bottom of bottle 12, illuminator 16 and detector 18 are positioned close to conveyor 14, typically within one eighth of an inch. As best illustrated in FIG. 3, a beam of light 35 from illuminator 16 is directed at and above the horizontal plane occupied by detector 18. As also illustrated in FIG. 3, the mean light path from lens 22 of illuminator 16 to fiber 28 of detector 18 is along path AE.

Although bottles and containers of various shapes may be inspected by system 10, the bottle 12 shown in FIGS. 2–5 has a base 36 with a convex bulge 37 in its bottom that causes liquid 34 near the bottom to form a concentric annular ring around convex bulge 37. Because base 36 has a smaller diameter than a main portion 38 of bottle 12, and illuminator 16 and detector 18 are positioned near the bottom of bottle 12, bottles 12 can be moved along conveyor 14 with no spacing—i.e., in contact with other bottles, with no interference by a bottle 12 with measurement taken by system 10 on an adjacent bottle 12.

A liquid supplier 39, positioned upstream of illuminator 16, adds a sufficient amount of liquid 34 to each bottle 12 to ensure that radiation emitted from illuminator 16 will encounter liquid in the bottom of each bottle 12. Generally, because extra liquid 34 does not affect the performance of system 10, liquid supplier 39 adds liquid 34 to each bottle 12 without regard to whether a bottle 12 already contains liquid. Addition of liquid 34 by supplier 39, which may be an injector timed to inject a pulse of liquid into the open top of each bottle 12 as it passes underneath the supplier 39, may assist in leaching contaminants from the bottle walls as well as ensuring the presence of a sufficient amount of liquid for detection. Typically, the liquid 34 supplied by liquid supplier 39 is water or a dilute aqueous solution. However, in some applications, other liquids could be used. For example, a liquid that changes color in the presence of an otherwise difficult to detect contaminant could be used to ease detection of that contaminant.

Figure 4:
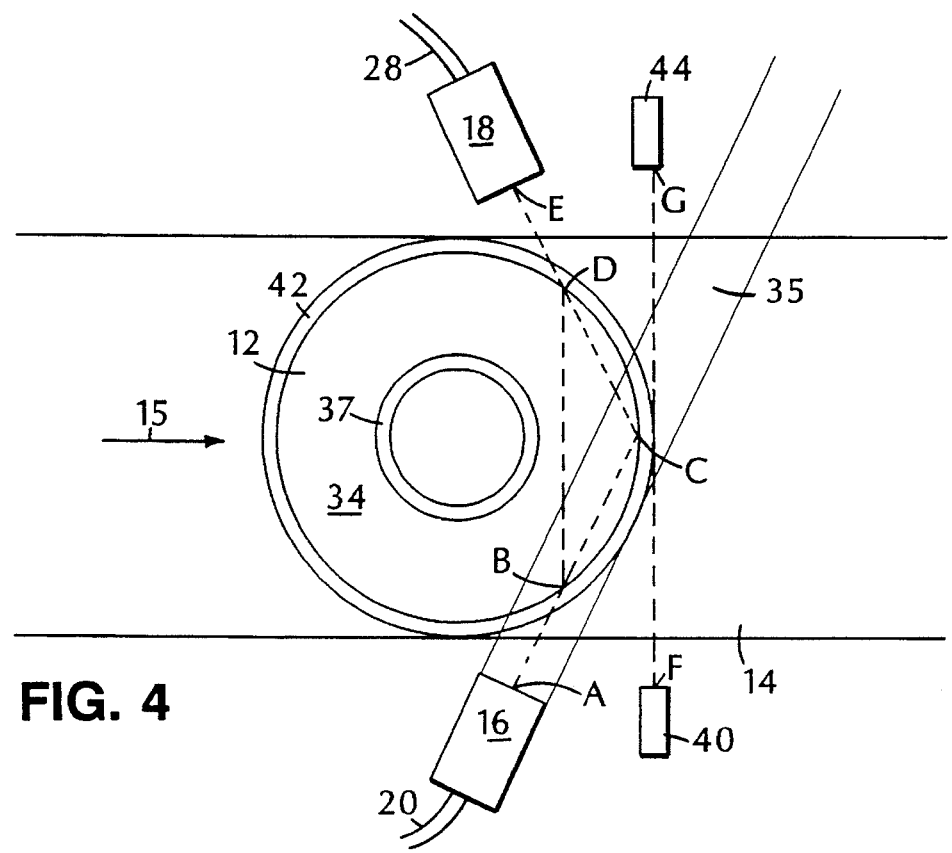
FIG. 4 is a cutaway top view taken along line 4—4 of FIG. 2 of a bottle and sensors of the system of FIG. 1 with the bottle in a first detection position.

With reference to FIG. 4, in which, for simplicity, only a single bottle 12 is shown, in operation of spectral contaminant detection system 10, a first position sensor 40 signals a processor 41 (FIG. 1) in control unit 26 when bottle 12 is positioned suitably to produce a first spectrum for liquid 34 and any contaminants contained therein. First position sensor 40 signals processor 41 when bottle 12 is positioned so that a portion of the radiant energy that reaches detector 18 from illuminator 16 travels along a path ABC, reflects from the inside surface of a wall 42 of bottle 12, and continues along a path CDE to detector 18. Because this position maximizes the length of the path that radiant energy takes through liquid 34, and thereby maximizes the absorption of radiant energy by liquid 34 and any contaminants contained therein, the measured spectrum is referred to as an absorption spectrum. Typically, illuminator 16 and detector 18 are positioned so that the angle ACE is within a range from 100°–140° with about 120° being most typical.

In actual operation, the portion of the radiant energy produced by illuminator 16 that actually reaches detector 18 travels by multiple paths that are significantly more complicated than the path described above. For example, the actual path is affected by reflection from wall 42 of bottle 12 and the interface between liquid 34 and air above liquid 34 in bottle 12. In addition, due to the presence of liquid 34, the radiant energy is refracted at points B and D, so that some of it travels approximately along a path BD before reaching detector 18. The radiant energy is affected also by scattering at wall 42 of bottle 12 and at convex bulge 37, and can travel along complicated paths that include several internal reflections within bottle 12.

First position sensor 40 signals processor 41 when the leading edge of a bottle 12 crosses a line FG between first position sensor 40 and a first light source 44. When bottle 12 crosses line FG, bottle 12 interrupts or otherwise causes a change in the level of light (radiation) from first light source 44 that reaches first position sensor 40. First position sensor 40 generates the signal to processor 41 in response to this change in the level of light.

Upon receiving the signal from first position sensor 40, processor 41 causes linear detection array 32 to record the spectrum produced by spectrometer 30 of the radiant energy detected by detector 18. Processor 41 then sequentially reads linear detection array 32 to generate a vector that represents the intensity of radiant energy received at each pixel of linear detection array 32, and stores the vector as an absorption spectrum associated with the bottle 12 being examined. Typically, each pixel of the absorption spectrum is represented by twelve bits. In the preferred embodiment, processor 41 is implemented using an Intel 486 processor running at sixty six megahertz.

Figure 5:
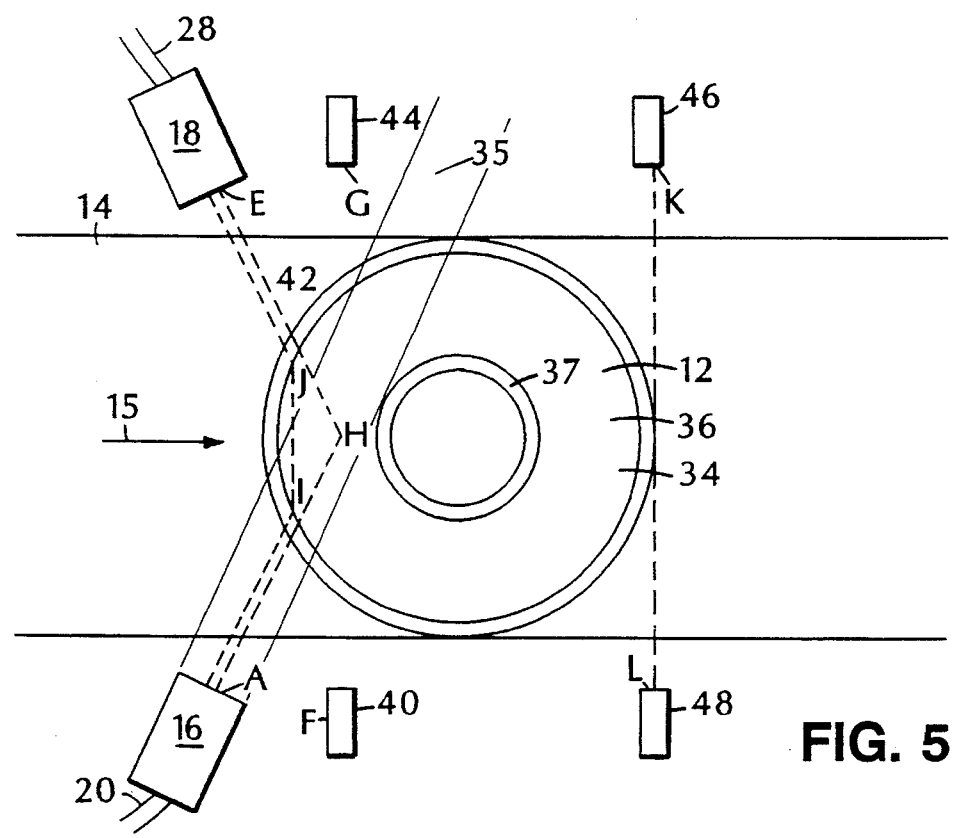
FIG. 5 is a similar view to that shown in FIG. 4, with the bottle in a second detection position.

With reference also to FIG. 5, in which, for simplicity, a single bottle is shown, a second position sensor 46 signals processor 41 when bottle 12 is positioned suitably to produce a second spectrum for liquid 34 and any contaminants contained therein. Second position sensor 46 signals processor 41 when bottle 12 is positioned so that radiant energy that reaches detector 18 from illuminator 16 travels approximately along a path AH, reflects from liquid 34 near the inner surface of wall 42, and continues approximately along a path HE to detector 18. Because most of the radiant energy reaching detector 18 does so by reflection rather than transmission, the measured spectrum for this second position of the bottle is referred to herein as a reflection spectrum.

It should be understood that the path of the radiant energy for the measurement at a second position of the bottle 12 is, like that of the first position, more complicated than illustrated in FIG. 5. For example, light could also travel along a path AI, refract at the interface between wall 42 and liquid 34, travel along a path IJ, refract at the interface between liquid 34 and wall 42, and travel along path JE to detector 18. Moreover, the intensity of the energy received by a detector 18 for the second position is typically lower than that received for the first position since, when bottle 12 is in the second position, most of the energy is transmitted beyond point H.

Second position sensor 46 signals processor 41 when a leading edge of bottle 12 crosses a line KL between second position sensor 46 and a second light source 48. Second position sensor 46 and second light source 48 are typically located downstream of first position sensor 40 and first light source 44 by slightly less than the diameter of bottle 12, and operate identically to first position sensor 40 and first light source 44. To prevent cross talk caused by first position sensor 40 responding to light produced by second light source 48, or by second position sensor 46 responding to light produced by first light source 44, the sensors and light sources are positioned with first position sensor 40 and second light source 48 on one side of conveyor 14, and second position sensor 46 and first light source 44 on the other side of conveyor 14. In an alternative approach to preventing cross talk, the sensor/light source pairs could be configured to respond to different frequencies of light.

Upon receiving the signal from second position sensor 46, processor 41 causes linear detection array 32 to record the spectrum produced by spectrometer 30 of the radiant energy detected by detector 18. Processor 41 then stores the recorded spectrum as a reflection spectrum associated with the bottle 12 being examined.

Processor 41 determines whether a bottle 12 contains contaminants by comparing the absorption and reflection spectra associated with the bottle 12 to a library of reference spectra associated with bottles containing acceptable substances. For example, for bottles to be filled with a beverage, acceptable substances would include water, beverage residue, and the aqueous solution supplied by liquid supplier 39. Processor 41 compares the spectra by computing either the Pearson's correlation or the Spearman's correlation for the vectors representing each spectrum.

Pearson's correlation, which is described, for example, in Pfaffenberger & Patterson, *Statistical Methods For Business and Economics*, p. 429 (1977, Richard D. Irwin, Inc., Homewood, Ill.), determines whether two vectors are related by a linear mapping, and r, the Pearson's correlation coefficient, is determined as:

$$r = \frac{\sum_{i=1}^{n} (x_i y_i)}{\sqrt{\sum_{i=1}^{n} (x_i)^2} \sqrt{\sum_{i=1}^{n} (y_i)^2}}$$

where $x_i$ equals the ith component of the vector X minus the average value of the components of the vector X, $y_i$ equals the ith component of the vector Y minus the average value of the components of the vector Y, and n equals the number of components in vector X or vector Y.

Spearman's correlation, which is described in Pfaffenberger & Patterson at p. 679, arranges the elements of each vector in rank order and determines whether two vectors have similar rank orders, and ρ, the Spearman's correlation coefficient, is determined as:

$$\rho = 1 - 6 \sum_{i=1}^{n} \frac{[R(X_i) - R(Y_i)]^2}{n(n^2 - 1)}$$

where $R(X_i)$ equals the rank of the ith component of the vector X relative to the other components of the vector X, $R(Y_i)$ equals the rank of the ith component of the vector Y relative to the other components of the vector Y, and each tied rank is assigned the average of the ranks that would have been assigned had there been no ties (e.g., if the fifth and sixth ranked components have equal values, they are each assigned a rank of 5.5).

If the spectra associated with the bottle 12 correlate within a predefined threshold—e.g., by greater than 90%—to a pair of reference spectra representing acceptable bottle content, processor 41 allows the bottle 12 to continue along conveyor 14 for filling or other testing. If not, processor 41 sends a signal to a suitable rejector 50, and rejector 50 responds by removing the bottle 12 from conveyor 14.

An advantage of comparing the spectra associated with a bottle 12 to reference spectra associated with bottles containing acceptable materials, rather than comparing with spectra associated with bottles containing unacceptable contaminants is that the former imposes less computational burden on processor 41. Moreover, detection accuracy of system 10 may be higher due to a reduced likelihood of failing to detect contaminants.

The computational burden is reduced because the number of acceptable reference spectra is typically quite limited, while, considering the number of potential contaminants and the various ways in which the contaminants can be combined, the number of unacceptable reference spectra may be virtually unlimited. For example, to detect contaminants in refillable polyethylene terephthalate cola bottles, it has been found that a library consisting of ten reference spectra—the absorption and reflection spectra associated with two liquid levels of water and three liquid levels of cola—is adequate.

The detection accuracy is higher because, unlike a system in which only bottles having spectra similar to reference spectra associated with known contaminants are rejected, system 10 is able to reject a bottle 12 that contains a previously unknown contaminant or a previously unknown combination of known contaminants.

Though comparison to acceptable reference spectra offers considerable advantages, the spectral contaminant detection system 10 can be configured to compare the spectra associated with unacceptable spectra or a combination of acceptable and unacceptable spectra. For example, to screen out, for testing or other purposes, only bottles containing particular contaminants such as a blue fabric softener or a green disinfectant, the spectra associated with the bottles could be compared to reference spectra associated with the particular contaminants. Similarly, if the spectra associated with a bottle containing a particular contaminant were close to the spectra of an uncontaminated bottle, it would be useful to accept the bottle only when its spectra are sufficiently similar to the spectra of the uncontaminated bottle and sufficiently different from the spectra of the contaminated bottle.

Lamp 24 may be a broadband source that produces radiant energy in a wavelength range from about 250 nanometers to about 2000 nanometers, which corresponds to visible light and infrared energy. Linear detection array 32 may produce spectra for the wavelength range from 320 to 1200 nanometers, which corresponds primarily to visible light. Within this range, for correlation purposes, the range from about 485 to about 600 nanometers has been found to be most useful for absorption spectra, and the range from about 350 to about 750 nanometers has been found to be most useful for reflection spectra.

In another embodiment, production of spectra for infrared wavelengths is emphasized, for example, to detect the presence of sugars in bottles to be filled with water (sugar absorbs radiation of wavelengths between 1300 and 1600 nanometers). In this embodiment, the spectrometer is modified by replacing the diffraction grating with one that operates in the desired wavelength range. Because infrared spectra can be used to identify almost all organic compounds, a system emphasizing the infrared spectra could be used as a general chemical detector.

The invention may be in the form of other embodiments. For example, though conveyor 14 is illustrated as a straight conveyor, system 10 could be applied effectively to a system in which bottles 12 are held in the periphery of a rotating wheel as they pass by illuminator 16 and detector 18. In this case, though bottles 12 would travel in an arc as they moved from the first position to the second position, their spectra would still be determined as illustrated in FIGS. 3 and 4.

In another variation, the contaminant detection system may generate and utilize only a single spectrum, such as an absorption spectrum or a reflection spectrum, for each bottle. Limited tests with a system utilizing an absorption spectrum alone or a reflection spectrum alone have generally shown lower overall accuracy in detection of contaminants, and have tended to produce more false positives, than a system generating and using both absorption and reflection spectra. However, a single spectrum may be adequate in certain applications. For example, an absorption spectrum may be sufficient for detection of contaminants in liquid/contaminant mixtures of high transmissivity.

Also, instead of varying the position of the bottle 12 relative to illuminator 16 and detector 18 to obtain different spectral characteristics, two or more sets of illuminators and detectors, having similar or different characteristics, and being operable simultaneously or sequentially, could be employed. For example, a first illuminator and detector pair could be configured and oriented to obtain a visible absorption spectrum while a second illuminator and detector pair is employed to obtain an infrared reflection spectrum.

What is claimed is:

1. A method of spectrally detecting a contaminant in a moving container, comprising:

storing reference spectral information related to at least one container having known contents, directing radiant energy at the moving container so that the radiant energy is modified by contents of the moving container to produce modified radiant energy, detecting a portion of the modified radiant energy that includes radiant energy that has travelled through the contents of the container in multiple paths of varying length, obtaining spectral information from the detected portion of modified radiant energy, comparing the spectral information obtained from the detected portion of modified radiant energy with the reference spectral information using correlation techniques, and indicating the presence of a contaminant based on the relationship between the spectral information obtained from the detected portion of modified radiant energy and the reference spectral information.

2. The method of claim 1 including:

detecting first and second portions of radiant energy modified by contents of the moving container, the first and second portions including radiant energy that has travelled through the contents of the container in multiple paths of varying length, obtaining first and second sets of spectral information, respectively, from the first and second detected portions of modified radiant energy, comparing the first and second sets of spectral information with the reference spectral information using correlation techniques, and indicating the presence of a contaminant based on the relationship between the first and second sets of spectral information and the reference spectral information.

3. The method of claim 2, wherein the moving container is located substantially in a first position when the first portion of radiant energy is detected and is located substantially in a second position when the second portion of radiant energy is detected, said method further comprising the step of moving the moving container from the first position to the second position.

4. The method of claim 1, wherein the spectral information obtained from the detected radiant energy measures absorption characteristics of the contents of the moving container.

5. The method of claim 1, wherein the spectral information obtained from the detected radiant energy measures reflection characteristics of the contents of the moving container.

6. The method of claim 2, wherein the first set of spectral information measures absorption characteristics of the contents of the moving container, and the second set of spectral information measures reflection characteristics of the contents of the moving container.

7. The method of claim 1, wherein said storing step includes storing reference spectral information related to at least one container having uncontaminated contents, and said indicating step includes indicating the presence of a contaminant when the spectral information obtained from the detected radiant energy does not match, within a predetermined threshold, reference spectral information related to a container having uncontaminated contents.

8. The method of claim 1, wherein said storing step includes storing reference spectral information related to at least one container having contaminated contents, and said indicating step includes indicating the presence of a contaminant when the spectral information obtained from the detected radiant energy matches, within a predetermined threshold, reference spectral information related to a container having contaminated contents.

9. The method of claim 1, wherein said storing step includes storing reference spectral information related to at least one container having uncontaminated contents and reference spectral information related to at least one container having contaminated contents, and wherein said indicating step includes indicating the presence of a contaminant when either (a) the spectral information obtained from the detected radiant energy does not match, within a predetermined threshold, reference spectral information related to a container having uncontaminated contents, or (b) the spectral information obtained from the detected radiant energy matches, within a predetermined threshold, reference spectral information related to a container having contaminated contents.

10. The method of claim 1, further comprising the step of adding a quantity of liquid to the moving container prior to said directing step, and wherein said directing step includes directing radiant energy at the moving container near the bottom thereof.

11. The method of claim 10, wherein said adding step includes adding less than about ten milliliters of liquid to the moving container.

12. The method of claim 11, wherein said adding step includes adding about five milliliters of liquid to the moving container.

13. The method of claim 1, wherein the spectral information relates to radiant energy having wavelengths that correspond to visible light.

14. The method of claim 1, wherein the spectral information obtained from the detected radiant energy relates to radiant energy having wavelengths that correspond to infrared energy.

15. The method of claim 1, wherein the spectral information obtained from the detected radiant energy relates to radiant energy having wavelengths that correspond to visible light and infrared energy.

16. The method of claim 1, wherein the moving container is a bottle.

17. The method of claim 16, wherein the bottle is made from plastic.

18. The method of claim 1, further comprising the step of rejecting the moving container following the indication of the presence of a contaminant.

19. A method of spectrally detecting a contaminant in a moving container, comprising the steps of:

storing reference spectral information related to at least one container having known contents, directing a first portion of radiant energy at the moving container so that the first portion of radiant energy is modified by the contents of the moving container near the bottom thereof to produce a first portion of modified radiant energy, directing a second portion of radiant energy at the moving container so that the second portion of radiant energy is modified by the contents of the moving container near the bottom thereof to produce a second portion of modified radiant energy, wherein the second portion of modified radiant energy is modified relative to the second portion of radiant energy in a different way the contents of the moving container than the first portion of modified radiant energy is modified relative to the first portion of radiant energy, obtaining a first set of spectral information related to the first portion of modified radiant energy, obtaining a second set of spectral information related to the second portion of modified radiant energy, comparing the first and second sets of spectral information with the reference spectral information using correlation techniques, and indicating the presence or absence of a contaminant based on the relationship of the first and second sets of spectral information to the reference spectral information.

20. The method of claim 19, wherein the moving container is located in a first position when the first portion of radiant energy is directed at the moving container and a second position when the second portion of radiant energy is directed at the moving container, said method further comprising the step of moving the moving container between the first and second positions.

21. The method of claim 19, wherein the first set of spectral information measures absorption characteristics of the contents of the moving container.

22. The method of claim 21, wherein the second set of spectral information measures reflection characteristics of the contents of the moving container.

23. The method of claim 19, wherein the first set of spectral information measures reflection characteristics of the contents of the moving container.

24. The method of claim 19, wherein said storing step includes storing reference spectral information related to at least one container having uncontaminated contents and said indicating step includes indicating the presence of a contaminant when the first and second sets of spectral information do not match, within a predetermined threshold, reference spectral information related to a container having uncontaminated contents.

25. The method of claim 19, wherein said storing step includes storing reference spectral information related to at least one container having contaminated contents and said indicating step includes indicating the presence of a contaminant when the first or second sets of spectral information match, within a predetermined threshold, reference spectral information related to a container having contaminated contents.

26. The method of claim 19, wherein said storing step includes storing reference spectral information related to at least one container having uncontaminated contents and reference spectral information related to at least one container having contaminated contents, and wherein said indicating step includes indicating the presence of a contaminant when either:

(a) the first and second sets of spectral information do not match, within a predetermined threshold, reference spectral information related to a container having uncontaminated contents, or (b) the first or second set of spectral information match, within a predetermined threshold, reference spectral information related to a container having contaminated contents.

27. The method of claim 19, further comprising the step of adding a quantity of liquid to the moving container prior to said directing step.

28. The method of claim 19, further comprising the step of rejecting the moving container following the indication of the presence of a contaminant.

29. The method of claim 19, wherein the moving container includes a convex bulge in its bottom, and wherein:

the step of directing a first portion of radiant energy comprises directing the first portion of radiant energy so that the first portion of radiant energy is modified by contents of the moving container below a top of the convex bulge, and the step of directing a second portion of radiant energy comprises directing the second portion of radiant energy so that the second portion of radiant energy is modified by contents of the moving container below the top of the convex bulge.

30. The method of claim 19, wherein the first portion of modified radiant energy includes a component of the first portion of radiant energy transmitted by the contents of the moving container.

31. The method of claim 30, wherein the second portion of modified radiant energy includes a component of the second portion of radiant energy reflected by the contents of the moving container.

32. A spectral contaminant detection system comprising:

an illuminator for directing radiant energy at a moving container;

a detector for detecting radiant energy from said illuminator that has been modified by the moving container and has passed through the moving container in multiple paths of varying length, and for producing spectral information related to the detected radiant energy; and a processor for comparing spectral information obtained from said detector with reference spectral information, and for indicating the presence of a contaminant based on the relationship between the obtained spectral information and the reference spectral information.

33. The system of claim 32, wherein said processor is an electronic computer operable to process information from at least 400 containers per minute.

34. The system of claim 32, wherein said detector includes an optical spectrometer for producing spectral information related to the detected radiant energy.

35. The system of claim 32, further comprising a first position sensor for signalling said processor to process spectral information from said detector when the moving container is in a first position.

36. The system of claim 35, further comprising a second position sensor for signalling said processor to process spectral information from said detector when the moving container is in a second position.

37. The system of claim 35, wherein said first position sensor is located relative to said illuminator and said detector so that during operation, when the moving container is in the first position, said processor obtains from said detector spectral information indicative of absorption characteristics of the contents of the moving container.

38. The system of claim 35, wherein said first position sensor is located relative to said illuminator and said detector so that during operation, when the moving container is in the first position, said processor obtains from said detector spectral information indicative of reflection characteristics of the contents of the moving container.

39. The system of claim 36, wherein said first position sensor is located relative to said illuminator and said detector so that during operation, when the moving container is in the first position, said processor obtains from said detector spectral information indicative of absorption characteristics of the contents of the moving container; and wherein said second position sensor is located relative to said illuminator and said detector so that during operation, when the moving container is in the second position, said processor obtains from said detector spectral information indicative of reflection characteristics of the contents of the moving container.

40. The system of claim 32, wherein the reference spectral information includes uncontaminated reference spectral information related to at least one container having uncontaminated contents, and wherein during operation said processor indicates the presence of a contaminant when the obtained spectral information does not match, within a predetermined threshold, the uncontaminated reference spectral information.

41. The system of claim 32, wherein the reference spectral information includes contaminated reference spectral information related to at least one container having contaminated contents, and wherein during operation said processor indicates the presence of a contaminant when the obtained spectral information matches, within a predetermined threshold, the contaminated reference spectral information.

42. The system of claim 32, wherein the reference spectral information includes uncontaminated reference spectral information related to at least one container having uncontaminated contents and contaminated reference spectral information related to at least one container having contaminated contents, and wherein during operation said processor indicates the presence of a contaminant when the obtained spectral information does not match, within a predetermined threshold, uncontaminated reference spectral information, or the obtained spectral information matches, within a predetermined threshold, contaminated reference spectral information.

43. The system of claim 32, wherein said illuminator and said detector are positioned such that radiant energy from said illuminator reaches said detector after passing through a region substantially near the bottom of the moving container.

44. The system of claim 43, wherein said illuminator and said detector are positioned such that radiant energy from said illuminator reaches said detector after passing through a region within about one inch of the bottom of the moving container.

45. The system of claim 32, wherein said illuminator and said detector are positioned relative to each other so that an angle formed by a longitudinal axis of said illuminator and a longitudinal axis of said detector is in the range from 100° to 140°.

46. The system of claim 45, wherein said illuminator and said detector are positioned relative to each other so that the angle formed by the longitudinal axis of said illuminator and the longitudinal axis of said detector is about 120°.

47. For use with a container inspection system having a conveyor for moving containers and a liquid supplier for adding uncontaminated liquid to each container, a spectral contaminant detector to be mounted near said conveyor at a location downstream of the liquid supplier, said spectral contaminant detector comprising:

an illuminator for directing radiant energy at a moving container;

a detector for detecting radiant energy from said illuminator that has been modified by the moving container and has passed through the moving container in multiple paths of varying length, and for producing spectral information related to the detected radiant energy; and a processor for comparing spectral information obtained from said detector with reference spectral information, and for indicating the presence of a contaminant based on the relationship between the obtained spectral information and the reference spectral information.

* * * * *